(12) United States Patent
Costella et al.

(10) Patent No.: US 11,623,029 B2
(45) Date of Patent: Apr. 11, 2023

(54) SPRAYABLE BARRIER AND METHODS FOR PREVENTION OF POSTOPERATIVE ADHESIONS

(71) Applicant: LUNA INNOVATIONS INCORPORATED, Roanoke, VA (US)

(72) Inventors: Lauren Anne Costella, Roanoke, VA (US); Michael J. Danilich, Roanoke, VA (US); Christopher K. Tison, Roanoke, VA (US); Patrick Cottler, Roanoke, VA (US)

(73) Assignee: LUNA LABS USA, LLC, Charlottesville, VA (US)

( * ) Notice: Subject to any disclaimer, the term of this patent is extended or adjusted under 35 U.S.C. 154(b) by 167 days.

(21) Appl. No.: 16/500,556

(22) PCT Filed: Mar. 28, 2018

(86) PCT No.: PCT/US2018/024716
§ 371 (c)(1),
(2) Date: Oct. 3, 2019

(87) PCT Pub. No.: WO2018/187111
PCT Pub. Date: Oct. 11, 2018

(65) Prior Publication Data
US 2020/0101203 A1 Apr. 2, 2020

Related U.S. Application Data

(60) Provisional application No. 62/482,294, filed on Apr. 6, 2017.

(51) Int. Cl.
*C08L 5/04* (2006.01)
*C08L 5/08* (2006.01)
(Continued)

(52) U.S. Cl.
CPC ............ *A61L 31/042* (2013.01); *C08K 3/105* (2018.01); *C08K 3/32* (2013.01); *C08L 5/04* (2013.01); *C08L 5/08* (2013.01); *C08K 2003/324* (2013.01)

(58) Field of Classification Search
CPC ......... A61L 31/042; C08K 3/105; C08K 3/32; C08L 5/04; C08L 5/08
See application file for complete search history.

(56) References Cited

U.S. PATENT DOCUMENTS

| | | | |
|---|---|---|---|
| 6,150,581 A * | 11/2000 | Jiang | C08L 5/08 602/50 |
| 6,638,917 B1 | 10/2003 | Li et al. | |
| 2013/0287817 A1* | 10/2013 | Drapeau | A61L 27/54 514/169 |

OTHER PUBLICATIONS

Shi et al. (Polyelectrolyte Complex Beads Composed of Water-Soluble Chitosan/Alginate: Characterization and Their Protein Release Behavior, Journal of Applied Polymer Science, vol. 100, 4614-4622, 2006) (Year: 2006).*

(Continued)

*Primary Examiner* — Melissa S Mercier
(74) *Attorney, Agent, or Firm* — Nixon & Vanderhye, P.C.

(57) ABSTRACT

Biologically acceptable surgical barrier materials are comprised of a polyelectrolytic complex of chitosan and sodium alginate. The chitosan is deacetylated in an amount between about 40 to about 60% and has a molecular weight (Mw) between 50,000 and 375,000 g/mol. The barrier materials may be formed by mixing a two-component material system whereby one component comprises the chitosan and a second component comprises the sodium alginate and directing such a mixture (e.g., via air-assisted spray nozzle) toward a surgical site in need of the material. A polyelectrolytic complex of the chitosan and sodium alginate will (Continued)

Mass loss data of samples submerged in PBS or lysozyme solutions suggests that there should be complete degradation of the sample within a 28 day window.

thereby form in situ. Suitable ionic cross-linkers may be provided in the individual components, e.g., calcium chloride with the chitosan component and sodium tripolyphosphate with the sodium alginate component.

17 Claims, 3 Drawing Sheets

(51) Int. Cl.
*A61L 15/12* (2006.01)
*A61L 26/00* (2006.01)
*A61L 31/04* (2006.01)
*C08K 3/105* (2018.01)
*C08K 3/32* (2006.01)

(56) References Cited

OTHER PUBLICATIONS

International Search Report for PCT/US2018/024716, dated Jul. 4, 2018, 4 pages.
Written Opinion of the ISA for PCT/US2018/024716, dated Jul. 4, 2018, 5 pages.
Tiwary et al., "Cross-linked chitosan films: effect of cross-linking density on swelling parameters", Pakistan journal of pharmaceutical sciences, Oct. 1, 2010, p. 443, XP55486349.

* cited by examiner

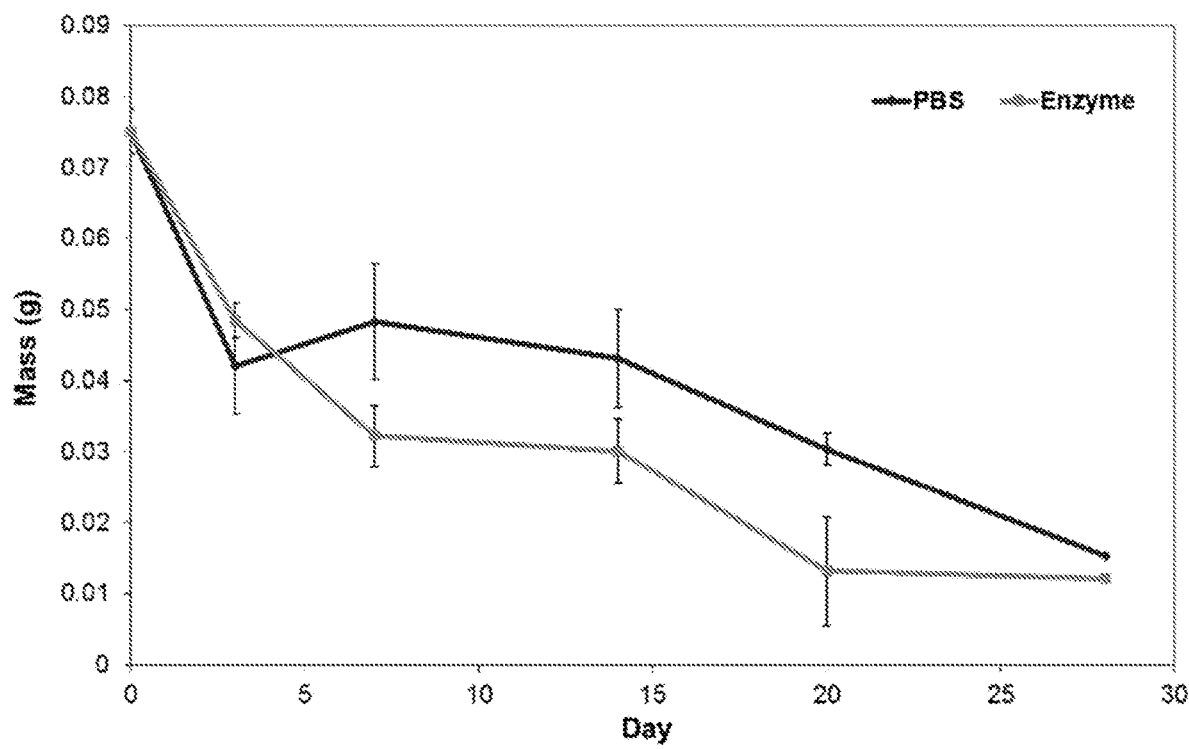
Figure 1. Mass loss data of samples submerged in PBS or lysozyme solutions suggests that there should be complete degradation of the sample within a 28 day window.

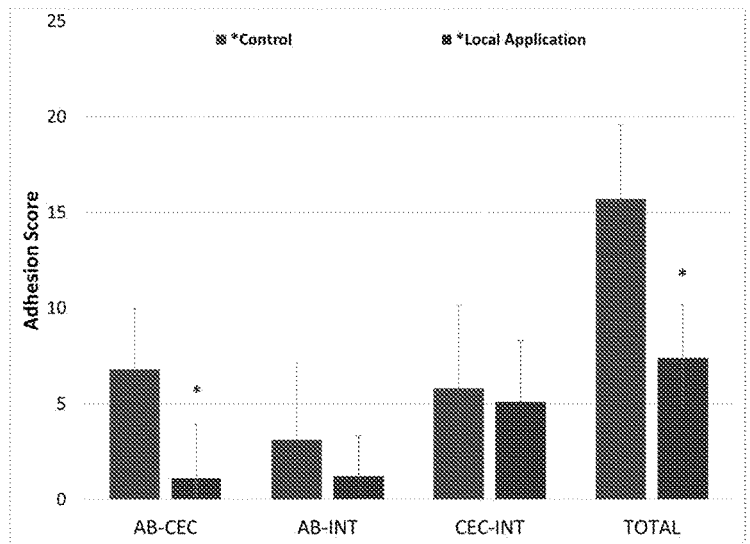

FIG. 2A

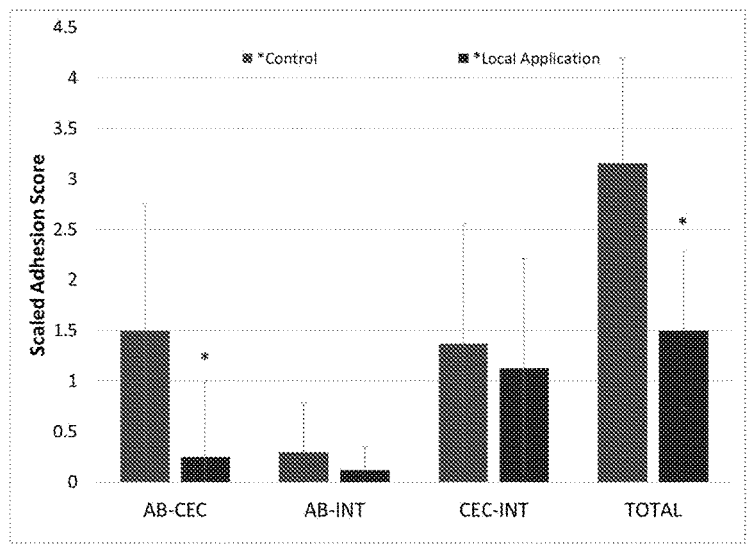

FIG. 2B

Figures 2A and 2B: The application of hydrogel using the air-assisted spray tip resulted in statistically significant decrease in the incidence and strength of primary adhesions, and no longer induces the increase in secondary adhesions seen in previous formulations. Results above present adhesion score (Fig. 2A) and scaled adhesion score (Fig. 2B) for n=10 rats per group. Statistical significance is defined as $p<0.05$ via the Wilcoxon Rank Sum Test.

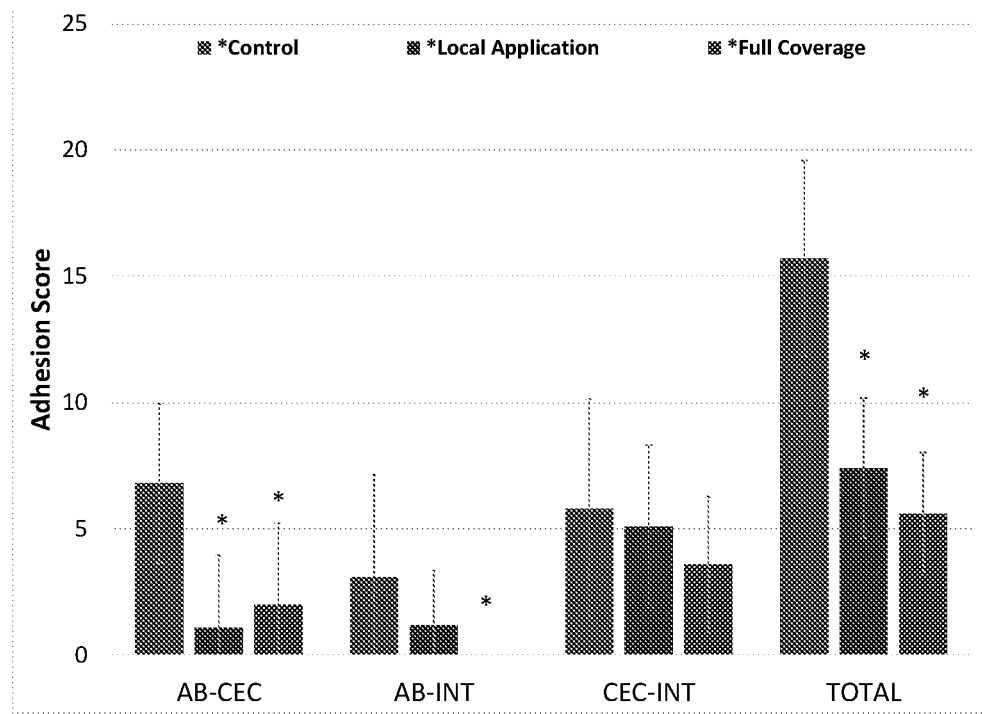

FIG. 3A

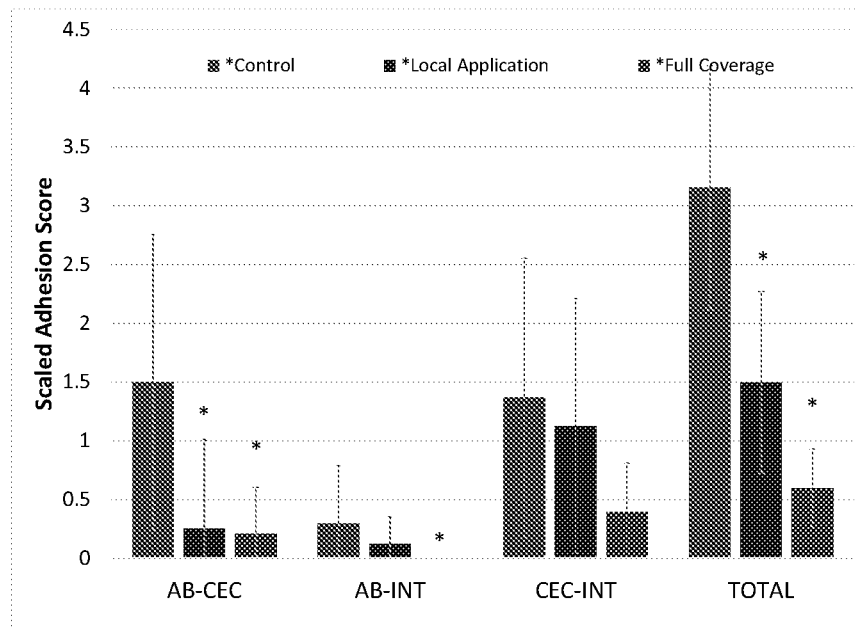

FIG. 3B

Figures 3A and 3B. Full application of the hydrogel, including those surfaces surrounding the injured tissue, results in a slight improvement, even as compared to the local application of the product. Results above present adhesion score (Fig. 3A) and scaled adhesion score (Fig. 3B) for n=10 rats per group. Statistical significance is defined as $p<0.05$ via the Wilcoxon Rank Sum Test.

SPRAYABLE BARRIER AND METHODS FOR PREVENTION OF POSTOPERATIVE ADHESIONS

CROSS-REFERENCE TO RELATED APPLICATION

This application is the U.S. national phase of International Application No. PCT/US2018/024716 filed 28 Mar. 2018, which claims priority benefits of U.S. Provisional Application Ser. No. 62/482,294 filed on Apr. 6, 2017, the entire contents of each of which are expressly incorporated hereinto by reference.

GOVERNMENT RIGHTS

This invention was made with Government support under NIH Phase I Program 2 R44 GM074373-01, NIH Phase II Program 2 R44 GM074373-02, NIH Phase I Program 1 R43 GM105142-01 and NIH Phase II Program 5 R44 GM105142-03. The Government has certain rights to the invention.

FIELD

The disclosed embodiments herein relate generally to sprayable materials that prevent adhesions form forming postoperatively at a surgical site.

BACKGROUND AND SUMMARY

Injury to tissue during surgery, trauma, infection, or other forms of inflammation will lead to the initiation of wound healing. If the fibrin matrix deposited during the initial stages of wound healing forms permanent contacts with neighboring tissue, it can form a fibrous strand that will capture fibroblasts and mesothelial cells until the fibrous strand develops into a firm, vascularized adhesion. Adhesion formation after surgery (e.g., intra-abdominal surgery) poses a significant health risk and has been cited as a leading cause of small bowel obstruction and female infertility. Methods to prevent these adhesions from forming are currently limited to inefficient liquid treatments that are quickly resorbed, or solid barrier films, which are difficult to place and are often restricted to use at the incision site, ultimately leaving the bulk of the abdominal contents unprotected.

It would therefore be highly desirable if a barrier material could be provided that would effectively prevent such tissue adhesions postoperatively at a surgical site. It is towards fulfilling such a need that the embodiments disclosed herein are directed.

In general, the embodiments disclosed herein are directed toward a sprayable hydrogel barrier that adheres to the internal tissues, e.g. of the patient's abdominal cavity, providing protection from adhesions to susceptible internal surfaces. The barrier gel disclosed herein is principally based on the interaction of two naturally-occurring biopolymers that together form a polyelectrolyte complex and is coupled with ionic crosslinkers to enhance the integrity of the resultant gel. The disclosed barrier gels are both biocompatible and biodegradable, and provide more complete protection than is available from currently marketed adhesion-prevention products. The barrier gel is applied by simultaneously spraying the two components over the injured or desiccated tissue. Upon interaction, a hydrogel begins to form that will ionically crosslink within less than 1 minute. The sprayable components are easily visualized during application due to the color in one of the components and may therefore be used satisfactorily for laparoscopic applications and open-abdominal procedures.

These and other aspects of the present invention will become more clear after careful consideration is given to the following detailed description of a presently preferred exemplary embodiment thereof.

BRIEF DESCRIPTION OF THE DRAWINGS

Reference will be made to the accompanying drawing Figures, wherein:

FIG. 1 is a graph showing mass loss data of hydrogel formulation samples submerged in PBS or lysozyme solutions which suggests that there should be complete degradation of the sample within a 28 day window;

FIGS. 2A and 2B are bar graphs showing the adhesion score (FIG. 2A) and scaled adhesion score (FIG. 2B) demonstrating that the local application (hydrogel material contained over two injury sites) of sprayable hydrogel material using an air-assisted spray tip results in statistically significant decrease in the incidence and strength of primary adhesions; and FIGS. 3A and 3B are bar graphs showing the adhesion score (FIG. 3A) and scaled adhesion score (FIG. 3B) demonstrating that the full application (hydrogel material applied over inured sites and neighboring tissue) of sprayable hydrogel material results in a slight improvement as compared to local application.

DETAILED DESCRIPTION

The sprayable barrier materials disclosed herein will necessarily include a chitosan component and a sodium alginate component. Each component may be provided separately of the other and then mixed together using a suitable atomizing spray system immediately prior to application at the desired tissue site. If mixture of the components is done by means of an atomizing spray system, then atmospheric air or an inert gas, e.g., carbon dioxide ($CO_2$), may be employed as an atomizing medium at an atomizing pressure of between about 5 psi to about 15 psi, typically 10 psi (+/−3 psi).

Each component of the sprayable barrier materials will be further described hereinbelow.

A. Chitosan Component

Chitosan is a linear polysaccharide derived from chitin, a biopolymer found in the exoskeleton of shrimp and crabs and also produced from certain fungal sources. Chitosan is generated from chitin by the conversion of N-acetyl groups to amino groups and is soluble in dilute acid solutions. The protonated amine group lends the chitosan a polycationic nature that may promote mucoadhesion to tissue and allows for controlled interaction with negatively charged ions.

The chitosan that may be employed in the practice of the barrier materials disclosed herein can be obtained commercially from a number of sources in powdered form. The commercially obtained chitosan is subjected to the following controlled processing in order to obtain chitosan having 40-60% deacetylation thereby providing the required water solubility.

For such processing, the chitosan is suspended in a 50% sodium hydroxide solution that has been purged with nitrogen and heated to 120° C. for 2.5 hours. The chitosan is then filtered and rinsed until neutral, resulting in 95% deacetylated chitosan. After this deacetylation treatment, the chitosan can be easily dissolved into dilute acetic acid (0.1 Molar)

at 2% w/v. Acetic anhydride is then added dropwise at 0.75% v/v and stirred for one hour to induce reacetylation of the chitosan to 40-60% deacetylation. Upon precipitation with the addition of 3-4× volumes of acetone, the chitosan is centrifuged to remove it from solution, and the pelleted treated chitosan product is lyophilized to produce a water-soluble powder.

Deacetylation and reacetylation processing may be accomplished using high molecular weight ($M_w$=310-375 kDa), medium molecular weight ($M_w$=190-310 kDa), and low molecular weight ($M_w$=50-190 kDa) chitosan. First-derivative UV-Vis characterization may be used to quantify the degree of acetylation throughout the chitosan treatment process. It has been determined that despite the different starting degrees of acetylation, the first deacetylation treatment brings substantially all chitosan samples to a level of 95% deacetylation, after which the 0.75% acetic anhydride reacetylation treatment consistently yields chitosan samples having a deacetylation level of 40-60%. Low $M_w$ chitosan may be difficult to precipitate and collect after reacetylation treatment. Medium $M_w$ and high $M_w$ chitosan are typically easier to collect. Preferably medium $M_w$ chitosan is subjected to the deacetylation-reacetylation treatment as it has been shown to form the hydrogels with the most desirable properties when dissolved at 0.5-1.5% w/v in deionized water. The chitosan product should have a molecular weight ($M_w$) between 50,000 and 375,000 g/mol.

The chitosan component and/or the sodium alginate component may be provided with suitable additives, for example, antifungal agents, coloring agents, cross-linking agents, therapeutic agents and the like. By way of example, sodium benzoate is preferably included within the two components to prevent mold growth in the solutions.

Calcium chloride may also be included in the chitosan component solution to serve as an ionic crosslinker to improve the gelation of the mixed barrier material. Calcium ions do not interact with chitosan in solution, but upon mixing with the sodium alginate component, the calcium will then act as a relatively strong ionic crosslinker of the alginate. This ionic cross-linking results in a gel with the physical properties necessary for keeping injured tissues physically separated from one another during healing. The calcium chloride may be present in the chitosan component solution in an amount less than 2 wt. %, based on total solution weight, e.g., 0 to 2 wt. %, with between about 1 to about 1.5 wt. % calcium chloride content being especially preferred for achieving the best crosslinking for gel physical properties without impeding degradation over a reasonable time frame (e.g., 14-28 days).

B. Alginate Component

Sodium alginate is the sodium salt of alginic acid, commonly referred to as alginate, an anionic polysaccharide found in the cell walls of algae. Alginate is a linear copolymer that is water soluble and associates with calcium to form an ionically crosslinked polymer network. Alginate is used throughout the food and drug industry as a thickening agent. The alginate should have a molecular weight of from about 75,000 to about 500,000 g/mol.

Alginate and chitosan associate with one another to form a polyelectrolyte complex in which the positive charges on the amino groups in chitosan associate with the negatively charged carboxylate groups on alginate to form a polymeric association and gelation reaction. The inclusion of an ionic crosslinker in the chitosan component solution (e.g., calcium chloride to interact with alginate) and sodium tripolyphosphate in the alginate component solution (e.g., to interact with chitosan) serves to further strengthen the integrity of the resultant gel. Sodium alginate is easily dissolved in water from 0-2% w/v with gentle heating and agitation. Used as a thickening agent, it has been found in these solutions to be most workable for the desired sprayable application when the sodium alginate component is present in the solution in an amount between about 0.25 to about 0.5% w/v.

Sodium tripolyphosphate (NaTPP) is the sodium salt of the polyphosphate penta-anion. With multiple negative charges present, NaTPP acts as a strong ionic crosslinker for chitosan, but does not interact with the alginate in solution prior to spraying. It has been determined that NaTPP concentrations between about 0.5 to about 1.5 wt. %, based on the total weight of the alginate component solution, form gels of desired integrity.

Methylene blue is a dark green powder that yields a blue solution when dissolved in water. Methylene blue is a component of a frequently prescribed urinary analgesic/anti-infective medicine and has been suggested to help in the prevention of adhesion formation after surgery. Methylene blue is used in the sprayable barrier materials as a visual aid, allowing the surgeon to visually determine where the gel has been sprayed and which tissues remain unprotected. The amount of methylene blue that may be employed as a visual marker in the alginate component solution may be present in an amount of 0.005 wt. % to 1.0 wt. %, typically 0.05 wt. % or less, e.g., about 0.01 wt. %, based on the total solution weight. At such levels, a sufficient blue color needed for visualization of the sprayed gel is provided. Other biologically acceptable colorants, e.g., dimethyl-methylene blue which provides a lighter purple color, may also satisfactorily be employed.

EXAMPLES

The following formulations shown in Table 1 below may be employed to obtain sprayable gel barrier materials in accordance with the invention:

TABLE 1

Sprayable hydrogel formulations (all percentages are weight percent based on the total weight of the final formulation or component solution as appropriate.)

| | | Syringe 1 | | | | Syringe 2 | | | | |
|---|---|---|---|---|---|---|---|---|---|---|
| Formulation | Final Formulation | Volume | Chitosan | Calcium Chloride | Solvent | Volume | Sodium Alginate | Methlyene Blue | NaTPP | Solvent |
| 1 (1-959-61) | 0.5% Chitosan 0.5% Alginate 0.05% | 3 mL | 1% (MMW 1xDA-RA, DD = 25) | | Deionized Water | 3 mL | 1% | 0.1% | | Deionized Water |

TABLE 1-continued Sprayable hydrogel formulations (all percentages are weight percent based on the total weight of the final formulation or component solution as appropriate.)

| | | Syringe 1 | | | | Syringe 2 | | | | |
|---|---|---|---|---|---|---|---|---|---|---|
| Formulation | Final Formulation | Volume | Chitosan | Calcium Chloride | Solvent | Volume | Sodium Alginate | Methlyene Blue | NaTPP | Solvent |
| 2 (2-959-62) | 0.5% Chitosan 0.25% Alginate 0.05% Methylene Blue | 3 mL | 1% (MMW 1xDA-RA, DD = 25) | | Deionized Water | 3 mL | 0.5% | 0.1% | | Deionized Water |
| 3 (3-959-63) | 0.5% Chitosan 0.25% Alginate 0.05% Methylene Blue 5% Calcium Chloride 5% NaTPP | 3 mL | 1% (MMW 1xDA-RA, DD = 25) | 10% | Deionized Water | 3 mL | 0.5% | 0.1% | 10% | Deionized Water |
| 4 (4-959-64) | 0.5% Chitosan 0.25% Alginate 0.05% Methylene Blue 0.5% Calcium Chloride 0.5% NaTPP | 3 mL | 1% (MMW 1xDA-RA, DD = 25) | 1% | Deionized Water | 3 mL | 0.5% | 0.1% | 1% | Deionized Water |
| 5 (5-959-86) | 0.5% Chitosan 0.25% Alginate 0.05% Methylene Blue 0.75% Calcium Chloride 0.75% NaTPP | 3 mL | 1% (HMW 1xDA-RA, DD = 46) | 1.5% | Deionized Water | 3 mL | 0.5% | 0.1% | 1.5% | Deionized Water |
| 6 (6-959-92) | 0.5% Chitosan 0.125% Alginate 0.05% Methylene Blue 0.75% Calcium Chloride 0.75% NaTPP | 3 mL | 1% (HMW 1xDA-RA, DD = 46) | 1.5% | Deionized Water | 3 mL | 0.25% | 0.1% | 1.5% | Deionized Water |
| 7 (7-959-93) | 0.5% Chitosan 0.25% Alginate 0.025% Methylene Blue 0.75% Calcium Chloride 0.75% NaTPP | 3 mL | 1% (HMW 1xDA-RA, DD = 46) | 1.5% | Deionized Water | 3 mL | 0.5% | 0.05% | 1.5% | Deionized Water |
| 8 (8-959-94) | 0.5% Chitosan 0.25% Alginate 0.025% Methylene | 3 mL | 1% (HMW 1xDA-RA, DD = 46) | 1.5% | Deionized Water | 3 mL | 0.5% | 0.05% | 1.5% | Deionized Water |

TABLE 1-continued

Sprayable hydrogel formulations (all percentages are weight percent based on the total weight of the final formulation or component solution as appropriate.)

| Formulation | Final Formulation | Syringe 1 | | | | Syringe 2 | | | | |
|---|---|---|---|---|---|---|---|---|---|---|
| | | Volume | Chitosan | Calcium Chloride | Solvent | Volume | Sodium Alginate | Methlyene Blue | NaTPP | Solvent |
| 9 (9-959-95) | Blue 0.75% Calcium Chloride 0.75% NaTPP 0.5% Chitosan 0.25% Alginate 0.025% Methylene Blue 0.75% Calcium Chloride 0.75% NaTPP | 3 mL | 1% Chitosan (MMW 1xDA-RA, DD = 47) | 1.5% | Deionized Water | 3 mL | 0.5% | 0.05% | 1.5% | Deionized Water |
| 10 (10-959-96) | 0.5% Chitosan 0.25% Alginate 0.025% Methylene Blue 0.75% Calcium Chloride 0.75% NaTPP | 3 mL | 1% (LMW 1xDA-RA, DD = 49) | 1.5% Calcium Chloride | Deionized Water | 3 mL | 0.5% | 0.05% | 1.5% | Deionized Water |
| 11 (11-959-108) | 0.5% Chitosan 0.25% Alginate 0.005% Methylene Blue 0.75% Calcium Chloride 0.75% NaTPP | 3 mL | 1% (MMW 1xDA-RA, DD = 47) | 1.5% | Deionized Water | 3 mL | 0.5% | 0.01% | 1.5% | Deionized Water |
| 12 (12-959-124) | 0.75% Chitosan 0.25% Alginate 0.005% Methylene Blue 0.75% Calcium Chloride 0.75% NaTPP | 1.5 mL | 1.5% (MMW 1xDA-RA) | 1.5% | Deionized Water | 1.5 mL | 0.5% | 0.01% | 1.5% | Deionized Water |
| 13 (13-959-126) | 0.75% Chitosan 0.25% Alginate 0.012% Methylene Blue 0.75% Calcium Chloride 1% NaTPP | 1.5 mL | 1.5% (MMW 1xDA-RA) | 1.5% | Deionized Water | 1.5 mL | 0.5% | 0.025% | 2% | Deionized Water |
| 14 (14-959-129) | 0.75% Chitosan 0.25% Alginate 0.012% Methylene Blue | 1.5 mL | 1.5% (HMW 1xDA-RA) | 1.5% | Deionized Water | 1.5 mL | 0.5% | 0.025% | 2% | Deionized Water |

TABLE 1-continued

Sprayable hydrogel formulations (all percentages are weight percent based on the total weight of the final formulation or component solution as appropriate.)

| | | Syringe 1 | | | | Syringe 2 | | | | |
|---|---|---|---|---|---|---|---|---|---|---|
| Formulation | Final Formulation | Volume | Chitosan | Calcium Chloride | Solvent | Volume | Sodium Alginate | Methlyene Blue | NaTPP | Solvent |
| 15 (15-959-130) | 0.75% Calcium Chloride 1% NaTPP 0.75% Chitosan 0.5% Alginate 0.012% Methylene Blue | 1.5 mL | 1.5% (HMW 1xDA-RA) | 1.5% | Deionized Water | 1.5 mL | 1% | 0.025% | 1.5% | Deionized Water |
| 16 (16-959-135) | 0.75% Calcium Chloride 0.75% NaTPP 0.75% Chitosan 0.5% Alginate 0.012% Methylene Blue | 1.5 mL | 1.5% (MMW 1xDA-RA) | 1.5% | Deionized Water | 1.5 mL | 1% | 0.025% | 1.5% | Deionized Water |
| 17 (17-995-45a) | 0.75% Calcium Chloride 0.75% NaTPP 0.25% Chitosan 0.125% Alginate 0.005% Methylene Blue | 1 mL | 0.5% (MMW 1xDA-RA) | 1.5% | Deionized Water | 1 mL | 0.25% | 0.01% | 1.5% | Deionized Water |
| 18 (18-995-45b) | 0.75% Calcium Chloride 0.75% NaTPP 0.25% Chitosan 0.125% Alginate 0.005% Methylene Blue | 1 mL | 0.5% (MMW 1xDA-RA) | 1% e | Deionized Water | 1 mL | 0.25% | 0.01% | 1.5% | Deionized Water |
| 19 (19-995-45c) | 0.5% Calcium Chloride 0.75% NaTPP 0.25% Chitosan 0.125% Alginate 0.005% Methylene Blue | 1 mL | 0.5% (MMW 1xDA-RA) | 0.5% | Deionized Water | 1 mL | 0.25% | 0.01% | 1.5% | Deionized Water |
| 20 (20-995-45d) | 0.25% Calcium Chloride 0.75% NaTPP 0.5% Chitosan 0.125% Alginate 0.005% Methylene Blue 0.75% | 1 mL | 1% n (MMW 1xDA-RA) | 1.5% | Deionized Water | 1 mL | 0.25% | 0.01% | 1.5% | Deionized Water |

TABLE 1-continued

Sprayable hydrogel formulations (all percentages are weight percent based on the total weight of the final formulation or component solution as appropriate.)

| Formulation | Final Formulation | Syringe 1 | | | | Syringe 2 | | | | |
|---|---|---|---|---|---|---|---|---|---|---|
| | | Volume | Chitosan | Calcium Chloride | Solvent | Volume | Sodium Alginate | Methlyene Blue | NaTPP | Solvent |
| 21 (21-995-45e) | Calcium Chloride 0.75% NaTPP 0.5% Chitosan 0.125% Alginate 0.005% Methylene Blue | 1 mL | 1% n (MMW 1xDA-RA) | 1% | Deionized Water | 1 mL | 0.25% | 0.01% | 1.5% | Deionized Water |
| 22 (22-995-45f) | 0.5% Calcium Chloride 0.75% NaTPP 0.5% Chitosan 0.125% Alginate 0.005% Methylene Blue | 1 mL | 1% (MMW 1xDA-RA) | 0.5% | Deionized Water | 1 mL | 0.25% | 0.01% | 1.5% | Deionized Water |
| 23 (23-995-46a) | 0.25% Calcium Chloride 0.75% NaTPP 0.25% Chitosan 0.125% Alginate 0.005% Methylene Blue | 1 mL | 0.5% (MMW 1xDA-RA) | 1.5% | Deionized Water | 1 mL | 0.25% | 0.01% | 1% | Deionized Water |
| 24 (24-995-46b) | 0.75% Calcium Chloride 0.5% NaTPP 0.25% Chitosan 0.125% Alginate 0.005% Methylene Blue | 1 mL | 0.5% (MMW 1xDA-RA) | 1% | Deionized Water | 1 mL | 0.25% | 0.01% | 1% | Deionized Water |
| 25 (25-995-46c) | 0.5% Calcium Chloride 0.5% NaTPP 0.25% Chitosan 0.125% Alginate 0.005% Methylene Blue | 1 mL | 0.5% (MMW 1xDA-RA) | 0.5% | Deionized Water | 1 mL | 0.25% | 0.01% | 1% | Deionized Water |
| 26 (26-995-46d) | 0.25% Calcium Chloride 0.5% NaTPP 0.5% Chitosan 0.125% Alginate 0.005% Methylene Blue 0.75% Calcium Chloride 0.5% NaTPP | 1 mL | 1% (MMW 1xDA-RA) | 1.5% | Deionized Water | 1 mL | 0.25% | 0.01% | 1% | Deionized Water |

TABLE 1-continued

Sprayable hydrogel formulations (all percentages are weight percent based on the total weight of the final formulation or component solution as appropriate.)

| | | Syringe 1 | | | | Syringe 2 | | | | |
| --- | --- | --- | --- | --- | --- | --- | --- | --- | --- | --- |
| Formulation | Final Formulation | Volume | Chitosan | Calcium Chloride | Solvent | Volume | Sodium Alginate | Methlyene Blue | NaTPP | Solvent |
| 27 (27-995-46e) | 0.5% Chitosan 0.125% Alginate 0.005% Methylene Blue 0.5% Calcium Chloride 0.5% NaTPP | 1 mL | 1% (MMW 1xDA-RA) | 1% | Deionized Water | 1 mL | 0.25% | 0.01% | 1% | Deionized Water |
| 28 (28-995-46f) | 0.5% Chitosan 0.125% Alginate 0.005% Methylene Blue 0.25% Calcium Chloride 0.5% NaTPP | 1 mL | 1% (MMW 1xDA-RA) | 0.5% | Deionized Water | 1 mL | 0.25% | 0.01% | 1% | Deionized Water |
| 29 (29-995-46g) | 0.25% Chitosan 0.125% Alginate 0.005% Methylene Blue 0.75% Calcium Chloride 0.25% NaTPP | 1 mL | 0.5% (MMW 1xDA-RA) | 1.5% | Deionized Water | 1 mL | 0.25% | 0.01% | 0.5% | Deionized Water |
| 30 (30-995-47a) | 0.25% Chitosan 0.125% Alginate 0.005% Methylene Blue 0.5% Calcium Chloride 0.25% NaTPP | 1 mL | 0.5% (MMW 1xDA-RA) | 1% | Deionized Water | 1 mL | 0.25% | 0.01% | 0.5% | Deionized Water |
| 31 (31-995-47b) | 0.25% Chitosan 0.125% Alginate 0.005% Methylene Blue 0.25% Calcium Chloride 0.25% NaTPP | 1 mL | 0.5% (MMW 1xDA-RA) | 0.5% | Deionized Water | 1 mL | 0.25% | 0.01% | 0.5% | Deionized Water |
| 32 (32-995-47c) | 0.5% Chitosan 0.125% Alginate 0.005% Methylene Blue 0.75% Calcium Chloride 0.25% NaTPP | 1 mL | 1% (MMW 1xDA-RA) | 1.5% | Deionized Water | 1 mL | 0.25% | 0.01% | 0.5% | Deionized Water |

TABLE 1-continued

Sprayable hydrogel formulations (all percentages are weight percent based on the total weight of the final formulation or component solution as appropriate.)

| Formulation | Final Formulation | Syringe 1 | | | | Syringe 2 | | | | |
|---|---|---|---|---|---|---|---|---|---|---|
| | | Volume | Chitosan | Calcium Chloride | Solvent | Volume | Sodium Alginate | Methlyene Blue | NaTPP | Solvent |
| 33 (33-995-47d) | 0.5% Chitosan 0.125% Alginate 0.005% Methylene Blue 0.5% Calcium Chloride 0.25% NaTPP | 1 mL | 1% (MMW 1xDA-RA) | 1% | Deionized Water | 1 mL | 0.25% | 0.01% | 0.5% | Deionized Water |
| 34 (34-995-47e) | 0.5% Chitosan 0.125% Alginate 0.005% Methylene Blue 0.25% Calcium Chloride 0.25% NaTPP | 1 mL | 1% (MMW 1xDA-RA) | 0.5% | Deionized Water | 1 mL | 0.25% | 0.01% | 0.5% | Deionized Water |
| 35 (35-995-47f) | 0.25% Chitosan 0.25% Alginate 0.005% Methylene Blue 0.75% Calcium Chloride 0.75% NaTPP | 1 mL | 0.5% (MMW 1xDA-RA) | 1.5% | Deionized Water | 1 mL | 0.5% | 0.01% | 1.5% | Deionized Water |
| 36 (36-995-47g) | 0.25% Chitosan 0.25% Alginate 0.005% Methylene Blue 0.5% Calcium Chloride 0.75% NaTPP | 1 mL | 0.5% (MMW 1xDA-RA) | 1% e | Deionized Water | 1 mL | 0.5% | 0.01% | 1.5% | Deionized Water |
| 37 (37-995-48a) | 0.25% Chitosan 0.25% Alginate 0.005% Methylene Blue 0.25% Calcium Chloride 0.75% NaTPP | 1 mL | 0.5% (MMW 1xDA-RA) | 0.5% | Deionized Water | 1 mL | 0.5% | 0.01% | 1.5% | Deionized Water |
| 38 (38-995-48b) | 0.5% Chitosan 0.25% Alginate 0.005% Methylene Blue 0.75% Calcium Chloride 0.75% NaTPP | 1 mL | 1% (MMW 1xDA-RA) | 1.5% | Deionized Water | 1 mL | 0.5% | 0.01% | 1.5% | Deionized Water |

TABLE 1-continued

Sprayable hydrogel formulations (all percentages are weight percent based on the total weight of the final formulation or component solution as appropriate.)

| Formulation | Final Formulation | Syringe 1 | | | | | Syringe 2 | | | | |
|---|---|---|---|---|---|---|---|---|---|---|---|
| | | Volume | Chitosan | Calcium Chloride | Solvent | | Volume | Sodium Alginate | Methlyene Blue | NaTPP | Solvent |
| 39 (39-995-48c) | 0.5% Chitosan 0.25% Alginate 0.005% Methylene Blue 0.5% Calcium Chloride 0.75% NaTPP | 1 mL | 1% (MMW 1xDA-RA) | 1% | Deionized Water | | 1 mL | 0.5% | 0.01% | 1.5% | Deionized Water |
| 40 (40-995-48d) | 0.5% Chitosan 0.25% Alginate 0.005% Methylene Blue 0.25% Calcium Chloride 0.75% NaTPP | 1 mL | 1% (MMW 1xDA-RA) | 0.5% | Deionized Water | | 1 mL | 0.5% | 0.01% | 1.5% | Deionized Water |
| 41 (41-995-48e) | 0.25% Chitosan 0.25% Alginate 0.005% Methylene Blue 0.75% Calcium Chloride 0.5% NaTPP | 1 mL | 0.5% (MMW 1xDA-RA) | 1.5% | Deionized Water | | 1 mL | 0.5% | 0.01% | 1% | Deionized Water |
| 42 (42-995-48f) | 0.25% Chitosan 0.25% Alginate 0.005% Methylene Blue 0.5% Calcium Chloride 0.5% NaTPP | 1 mL | 0.5% (MMW 1xDA-RA) | 1% | Deionized Water | | 1 mL | 0.5% | 0.01% | 1% | Deionized Water |
| 43 (43-995-48g) | 0.25% Chitosan 0.25% Alginate 0.005% Methylene Blue 0.25% Calcium Chloride 0.5% NaTPP | 1 mL | 0.5% (MMW 1xDA-RA) | 0.5% | Deionized Water | | 1 mL | 0.5% | 0.01% | 1% | Deionized Water |
| 44 (44-995-49a) | 0.5% Chitosan 0.25% Alginate 0.005% Methylene Blue 0.75% Calcium Chloride 0.5% NaTPP | 1 mL | 1% (MMW 1xDA-RA) | 1.5% | Deionized Water | | 1 mL | 0.5% | 0.01% | 1% | Deionized Water |
| 45 (45-995-49b) | 0.5% Chitosan 0.25% Alginate | 1 mL | 1% (MMW 1xDA-RA) | 1% | Deionized Water | | 1 mL | 0.5% | 0.01% | 1% | Deionized Water |

TABLE 1-continued

Sprayable hydrogel formulations (all percentages are weight percent based on the total weight of the final formulation or component solution as appropriate.)

| | | Syringe 1 | | | | Syringe 2 | | | | |
|---|---|---|---|---|---|---|---|---|---|---|
| Formulation | Final Formulation | Volume | Chitosan | Calcium Chloride | Solvent | Volume | Sodium Alginate | Methlyene Blue | NaTPP | Solvent |
| 46 (46-995-49c) | 0.005% Methylene Blue 0.5% Calcium Chloride 0.5% NaTPP 0.5% Chitosan 0.25% Alginate | 1 mL | 1% (MMW 1xDA-RA) | 0.5% | Deionized Water | 1 mL | 0.5% | 0.01% | 1% | Deionized Water |
| 47 (47-995-49d) | 0.005% Methylene Blue 0.25% Calcium Chloride 0.5% NaTPP 0.25% Chitosan 0.25% Alginate | 1 mL | 0.5% (MMW 1xDA-RA) | 1.5% | Deionized Water | 1 mL | 0.5% | 0.01% | 0.5% | Deionized Water |
| 48 (48-995-49e) | 0.005% Methylene Blue 0.75% Calcium Chloride 0.25% NaTPP 0.25% Chitosan 0.25% Alginate | 1 mL | 0.5% (MMW 1xDA-RA) | 1% | Deionized Water | 1 mL | 0.5% | 0.01% | 0.5% | Deionized Water |
| 49 (49-995-49f) | 0.005% Methylene Blue 0.5% Calcium Chloride 0.25% NaTPP 0.25% Chitosan 0.25% Alginate | 1 mL | 0.5% (MMW 1xDA-RA) | 0.5% | Deionized Water | 1 mL | 0.5% | 0.01% | 0.5% | Deionized Water |
| 50 (50-995-49g) | 0.005% Methylene Blue 0.25% Calcium Chloride 0.25% NaTPP 0.5% Chitosan 0.25% Alginate | 1 mL | 1% (MMW 1xDA-RA) | 1.5% Calcium Chloride | Deionized Water | 1 mL | 0.5% | 0.01% | 0.5% | Deionized Water |
| 51 (51-995-50a) | 0.005% Methylene Blue 0.75% Calcium Chloride 0.25% NaTPP 0.5% Chitosan 0.25% Alginate 0.005% | 1 mL | 1% (MMW 1xDA-RA) | 1% | Deionized Water | 1 mL | 0.5% | 0.01% | 0.5% | Deionized Water |

TABLE 1-continued

Sprayable hydrogel formulations (all percentages are weight percent based on the total weight of the final formulation or component solution as appropriate.)

| | | Syringe 1 | | | | Syringe 2 | | | | |
|---|---|---|---|---|---|---|---|---|---|---|
| Formulation | Final Formulation | Volume | Chitosan | Calcium Chloride | Solvent | Volume | Sodium Alginate | Methylene Blue | NaTPP | Solvent |
| 52 (52-995-50b) | Methylene Blue 0.5% Calcium Chloride 0.25% NaTPP 0.5% Chitosan 0.25% Alginate 0.005% Methylene Blue 0.25% Calcium Chloride 0.25% NaTPP | 1 mL | 1% (MMW 1xDA-RA) | 0.5% | Deionized Water | 1 mL | 0.5% | 0.01% | 0.5% | Deionized Water |
| 53 (53-989-06) | 0.25% Chitosan 0.125% Alginate 0.005% Methylene Blue 0.5% Calcium Chloride 0.5% NaTPP 0.1% Sodium Benzoate | 1 mL | 0.5% (MMW 1xDA-RA) | 1% | Deionized Water + 0.1% Sodium Benzoate | 1 mL | 0.25% | 0.01% | 1% | Deionized Water + 0.1% Sodium Benzoate |
| 54 (54-1089-37) | 0.375% Chitosan 0.125% Alginate 0.0025% Methylene Blue 0.375% Calcium Chloride 0.375% NaTPP | 1-3 mL | 0.75% (MMW 1xDA-RA) | 0.75% | Deionized Water | 1-3 mL | 0.25% | 0.005% | 0.75% | Deionized Water |

As shown in Table 1 above, formulations range in final chitosan content from 0.25% to 0.75%, alginate content from 0.5% to 0.125%, calcium chloride content from 5% to 0.25%, sodium tripolyphosphate content from 5% to 0.25%, and methylene blue content from 0.05% to 0.005%. Additional additives included dimethylemthylene blue and sodium benzoate. Formulations 12-959-124, 53-989-06, and 54-1089-37 in Table 1 were further tested in animal models discussed below.

Example I—In Vitro Testing

For the first round of analysis of each tested formulation, samples were injected into plastic weigh dishes and allowed to undergo gelation and crosslinking for one minute prior to analysis. The gel was then analyzed for both cohesive and adhesive properties by tilting the weigh dish and prodding at the formed gel with tweezers.

Tissue adhesion properties were assessed by spraying the gel over two pieces of fresh bovine liver warmed to 37° C. The gel was allowed to crosslink for 1 minute before the two gel-coated surfaces were brought in contact with one another. Gentle pressure was applied to the top surface as it was slid laterally across the surface of the bottom piece of tissue. The interaction between the two layers of gel was analyzed to assess the gel's cohesion to itself and adhesion to the tissue to which it was applied. It was determined that while high concentrations (1.5%) of crosslinkers provided a more robust gel with greater cohesion, it failed to stimulate increased tissue adhesion and the gel would drag off the surface of the liver with pressure and collect into a large clump. Thinner formulations with better spray application remained mostly in place, with at least a thin coating of the applied gel remaining over each of the tissue surfaces.

The cytocompatibility of the two unreacted components, the mixed unreacted runoff following spray and gelation, and the final gel of Formulation 12-959-124 (1.5% MMW RA-DA Chitosan+1.5% CaCl2, 0.5% Alginate+0.01% Methylene Blue+1.5% NaTPP, and 0.5% Alginate+0.1% Sodium Benzoate+1.5% NaTPP). Solutions were sterile filtered prior to testing. 500 μL of each solution sample was injected into the center of a 6 well plate containing L929 mouse fibroblast cells seeded 24 hours previously with 100,000 cells/well. To create the gels, 250 μl of each solution were injected into a microcentrifuge tube and the resulting gel was placed in the center of the cell-seeded well using sterile tweezers. Cells were imaged 4 days after the addition of the components, and it was determined that while the cells in contact with the final gels were confluent and growing readily, those in contact with the alginate component alone were surprisingly sparse. Despite this lack of confluence in the unreacted alginate samples, there were no signs of inherent toxicity in these samples.

Degradation of Formulation 12-959-124 was tested by injecting 3 mL of gel into conical tubes containing PBS (control) or 1.5 μg/mL lysozyme solution. Samples were stored at 37° C. and analyzed weekly over a 28 day period for mass loss. As is suggested by the graph of FIG. 1, degradation and clearance from the body is expected within 28 days.

Example 2—In Vivo Testing

Preliminary testing was performed using formulations deemed most promising in in vitro experimentation in previously sacrificed pigs prior to proceeding to in vivo experimentation on live animals. Briefly, the surface of the stomach of a pig that had been sacrificed for previous experimentation was exposed and coated with various test formulations. Gel solutions were allowed to set for 1-2 minutes, after which the surface of the stomach was rubbed against neighboring tissues to simulate normal peristaltic movements. The gel was assessed qualitatively for its ability to remain in place after contacting surrounding tissue.

After the first round of porcine testing, Formulation 12-959-124 was selected for further testing in the in vivo rat model. The formulation was applied as using a spray applicator assembly designed for the application of biomedical materials and commercially available from Nordson Corporation provided with suitable spray tips (i.e., either a manual applicator system using mix tip SA-3674 or an air-assisted application system using mix tip SA-3652).

(i) Animal Model Protocol:

In vivo testing was performed by an experienced animal surgeon at the University of Virginia using an established protocol examining adhesion formation between injured abdominal wall and cecum surfaces. Rats were anesthetized using Ketamine/Xlyazine and matching defects were created on the abdominal wall and cecum surfaces. The abdominal wall injury was created by removing the peritoneum and associated muscle fibers within a 1 cm×2 cm area. The cecum defect was created by removing the serosal sheath in a matching 1 cm×2 cm area with 100 wipes using a piece of gauze. The wounded areas were desiccated by exposure to air for 15 minutes, and the animals were then left untreated (control) or treated with the hydrogel formulation in accordance with the invention sprayed over each of the injured sites until visual coverage was achieved. The gel was allowed to crosslink for approximately one minute prior to closure. Following treatment, the cecum was placed adjacent to the abdominal wall injury site and the incision was closed with sutures and staples. Rats were bandaged and housed individually until analysis.

Animals were sacrificed and analyzed at Day 7 based on the adhesion scoring system shown in Table 2 below.

TABLE 2

| Adhesion Scoring Scale | | | |
|---|---|---|---|
| Score | Extent | Tenacity | Type |
| 0 | 0% | None | none |
| 1 | <25% | Easily lysed | filmy, no vessels |
| 2 | 25-50% | Lysed w/ Traction | opaque, no vessels |
| 3 | 50-75% | Requires dissection | opaque, small vessels |
| 4 | >75% | | opaque, large vessels |

Analysis of the sacrificed animal was carried out by carefully opening the abdominal cavity to prevent the disruption of any adhesions that may have formed. The implant site was observed macroscopically for evidence of gel residence, reactivity of tissue, inflammatory response, and adhesion formation between the cecum, abdominal wall, and surrounding mesentery, viscera, and fat. Though the model is designed to only examine adhesion formation between the abdominal wall and cecum surfaces (Ab-Cec, primary adhesions), the adhesions that occurred between the abdominal wall and other internal tissues (Ab-Int), and cecum to other internal tissue (Cec-Int), known as secondary adhesions, were also assessed. The adhesions for each pair of tissue were characterized according to the extent of wounded surface covered (score 0-4), the tenacity of the adhesion formed (score 0-3), and the type of adhesion formed (0-4). Therefore, a maximum score of 11 was possible for each tissue pair combination. The "scaled adhesion score" for each tissue group was also examined in which the actual percentage of the injured surface covered by the adhesion (0-1) was multiplied by the tenacity score (0-3) of the adhesion. This analysis resulted in a continuous scoring system between 0-3 for each tissue group and enabled a more comprehensive understanding of the actual size and strength of the adhesions that formed from various treatment groups.

(ii) Preliminary in vivo testing:

Preliminary animal testing was conducted using Formulation 12-959-124 (a 1:1 mixture of 1.5% MMW 1×DA-RA Chitosan/1.5% Calcium Chloride and 0.5% Sodium Alginate/0.01% Methylene Blue/1.5% Sodium Tripolyphosphate) sprayed over the injured tissue surfaces using a manual spray applicator with mix tip SA-3674 from Nordson Corporation. Animals received 1-3 mL of each gel sprayed over each injury site. There were no indications of immune response or tissue reaction to the implanted product over the seven day test period Untreated control animals demonstrated consistent formation of the primary adhesion. The average primary adhesion score for the controls was 5.75±2.43, and the average total adhesion score was 7.63±3.50. Those samples treated with the sprayable hydrogel formulation in accordance with the invention demonstrated a statistically significant decrease in primary adhesion formation, with an average primary adhesion score of 1.63±2.60. There was, however, a significant increase in secondary adhesion formation to the injured cecum surface, with a score of 3.50±2.19. The total adhesion score for treated animals was 5.44±2.63. All of these scores are presented below in Table 1 below.

TABLE 1

Average adhesion score ± standard deviation for animals in the full study

| | Ab-Cec | Ab-Int | Cec-Int | Total |
|---|---|---|---|---|
| Control (n = 8) | 5.75 ± 2.43 | 1.38 ± 1.19 | 0.5 ± 0.93 | 7.63 ± 3.50 |
| Spray (n = 16) | 1.63 ± 2.60 | 0.31 ± 0.87 | 3.5 ± 2.19 | 5.44 ± 2.63 |

The data presented in Table 1 indicate that treatment with the sprayable hydrogel according to the invention decreases the incidence and severity of adhesions that form between the abdominal wall and cecum injury sites. As noted previously, an increase in the incidence of secondary adhesions was observed between the cecum surface and other internal tissues. This is hypothesized to be due to the fact that a majority of the control animals formed the primary adhesion between the abdominal wall and cecum injury sites, leaving these tissues unable to form secondary adhesions because the injured sites are already occupied. By effectively preventing the primary adhesion from forming with the application of the hydrogel material, this surface has been freed for the formation of secondary adhesions. There is no suitable control for secondary adhesion formation.

(ii) Secondary In Vivo Testing:

Using the air-assisted spray tip SA-3652 applied at 10 psi, only 0.5-1.5 mL of the hydrogel could be delivered and still provide sufficient coverage over both injury sites. This reduction in the total amount of hydrogel (from 2-6 mL down to 0.5-1.5 mL) required to protect the injured tissue surfaces successfully resulted in a decrease in primary adhesion formation and no longer increased the likelihood of secondary adhesions forming on the cecum surface as was typical in previous applications during preliminary in vivo testing. Statistical analysis as shown in FIGS. 2A and 2B showed that the decrease in total and scaled adhesion scores for both the primary and total adhesions are statistically significant.

In an effort to better mimic actual in vivo application, "full application" of the hydrogel has been investigated. In a full application, the hydrogel material is sprayed over both injured surfaces as well as on the surfaces immediately surrounding each injury site for a total volume of 1-2 mL hydrogel applied per animal (using the air assist spray tip). This increased application resulted in improved protection of the abdominal wall, eliminating the incidence of secondary adhesions there and maintaining a statistically significant decrease in the incidence and strength of primary adhesions. Secondary adhesions to the cecum surface remain statistically unchanged as compared to controls, and total adhesion scores were again reduced significantly (See FIGS. 3A and 3B).

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. A method of forming a biologically acceptable barrier material at a surgical site comprising:
   (i) providing a barrier material system comprised of separate first and second solutions, wherein:
      (a) the first solution comprises:
         (a1) a water soluble chitosan which is deacetylated in an amount between about 40% to about 60%, and
         (a2) calcium chloride as a first ionic cross-linker, and
      (b) the second solution comprises:
         (b1) sodium alginate, and
         (b2) sodium tripolyphosphate (NaTPP) as a second ionic cross-linker,
   (ii) mixing the first and second solutions of the barrier material system in a mixing chamber to form a sprayable polyelectrolytic hydrogel complex of the chitosan and sodium alginate,
   (iii) immediately after the mixing according to step (ii), expelling the sprayable polyelectrolytic hydrogel complex from the mixing chamber and directing the sprayable polyelectrolytic hydrogel complex expelled from the mixing chamber toward the surgical site, and
   (iv) allowing a surgical barrier material formed of the polyelectrolytic hydrogel complex of the chitosan and sodium alginate to form in situ at the surgical site by allowing the sodium alginate in the second solution to be cross-linked by the first ionic cross-linker in the first solution and the chitosan in the first solution to be cross-linked by the second ionic cross-linker in the second solution.

2. The method according to claim 1, wherein steps (ii) and (iii) are practiced using a manual or a gas-assisted mixing and spray applicator.

3. The method according to claim 1, wherein steps (ii) and (iii) are practiced with a gas-assisted mixing and spray applicator using atmospheric air or carbon dioxide gas at an atomizing pressure of between about 5 psi to about 15 psi.

4. The method according to claim 1, wherein at least one of the first and second solutions comprises a biologically acceptable colorant.

5. The method according to claim 4, wherein the second solution comprises the colorant, and wherein the colorant is present in the second solution in an amount of 0.005 wt. % to 1.0 wt. %, based on total weight of the second solution.

6. The method according to claim 1, wherein the first solution comprises 1 to 2 wt. %, based on the total weight of the first solution, of calcium chloride as the first ionic crosslinker.

7. The method according to claim 6, wherein the second solution comprises between about 0.5 to about 1.5 wt. %, based on the total weight of the second solution, of the sodium tripolyphosphate as the second ionic crosslinker.

8. The method according to claim 1, wherein step (iv) comprises forming the surgical barrier of the polyelectrolytic hydrogel complex of the chitosan and sodium alginate in less than about 1 minute.

9. The method according to claim 1, wherein step (i) comprises providing the first and second solutions in respective syringes.

10. The method according to claim 1, wherein step (ii) comprises concurrently passing the first and second solutions through a mixing tip to thereby mix the first and second solutions within the mixing tip to thereby form the sprayable polyelectrolytic hydrogel complex of the chitosan and sodium alginate.

11. The method according to claim 10, wherein step (iii) comprises expelling the sprayable polyelectrolytic hydrogel complex of the chitosan and sodium alginate from the mixing tip toward the surgical site.

12. The method according to claim 1, wherein the chitosan has a molecular weight (Mw) between 50,000 and 375,000 g/mol.

13. The method according to claim 12, wherein the first solution comprises 1 to 2 wt. %, based on the total weight of the first solution, of calcium chloride as the first ionic crosslinker.

14. The method according to claim 13, wherein the second solution comprises between about 0.5 to about 1.5 wt. %, based on the total weight of the second solution, of the sodium tripolyphosphate as the second ionic crosslinker.

15. The method according to claim 14, wherein the second solution comprises 0.25 to about 0.5% w/v of the sodium alginate, and wherein the sodium alginate has a molecular weight of from about 75,000 to about 500,000 g/mol.

16. The method according to claim 15, wherein at least one of the first and second solutions comprises a biologically acceptable colorant.

17. The method according to claim 16, wherein the second solution comprises the colorant, and wherein the colorant is present in the second solution in an amount of 0.005 wt. % to 1.0 wt. %, based on total weight of the second solution.

* * * * *